(12) United States Patent
Ishikawa et al.

(10) Patent No.: US 10,429,315 B2
(45) Date of Patent: Oct. 1, 2019

(54) IMAGING APPARATUS AND IMAGING METHOD

(71) Applicant: Samsung Electronics Co., Ltd., Suwon-si (KR)

(72) Inventors: Akio Ishikawa, Yokohama (JP); Ken Ozawa, Yokohama (JP); Kwang-Soo Kim, Pyeongtaek-si (KR); Sean Park, Yongin-si (KR); Mitsunori Numata, Yokohama (JP)

(73) Assignee: SAMSUNG ELECTRONICS CO., LTD., Samsung-ro, Yeongtong-gu, Suwon-si, Gyeonggi-do (KR)

( * ) Notice: Subject to any disclaimer, the term of this patent is extended or adjusted under 35 U.S.C. 154(b) by 0 days.

(21) Appl. No.: 16/037,088

(22) Filed: Jul. 17, 2018

(65) Prior Publication Data

US 2019/0025226 A1    Jan. 24, 2019

(30) Foreign Application Priority Data

Jul. 18, 2017  (JP) ................................ 2017-138724
Oct. 18, 2017  (KR) ........................ 10-2017-0135454

(51) Int. Cl.
| G01N 21/00 | (2006.01) |
| G01N 21/88 | (2006.01) |
| G02B 27/42 | (2006.01) |
| G06T 7/00 | (2017.01) |
| G01N 21/956 | (2006.01) |

(52) U.S. Cl.
CPC ....... G01N 21/8806 (2013.01); G01N 21/956 (2013.01); G02B 27/42 (2013.01); G06T 7/0002 (2013.01); *G01N 2201/06* (2013.01); *G06T 2207/10152* (2013.01)

(58) Field of Classification Search
CPC .......... G01N 21/9501; G01N 21/8806; G01N 21/94; G01N 21/956; G01N 21/88
USPC ....................................... 356/237.1
See application file for complete search history.

(56) References Cited

U.S. PATENT DOCUMENTS

| 6,248,988 B1 | 6/2001 | Krantz |
| 7,385,693 B2 | 6/2008 | Namiki |
| 9,513,228 B2 | 12/2016 | Shibata et al. |
| 2010/0260409 A1 | 10/2010 | Ben-Levy |
| 2011/0060232 A1* | 3/2011 | Lin ...................... A61B 3/1233 |
| | | 600/504 |

(Continued)

FOREIGN PATENT DOCUMENTS

| JP | 05209841 | 8/1993 |
| JP | 11201909 | 7/1999 |
| JP | 5725501 | 5/2015 |

*Primary Examiner* — Md M Rahman
(74) *Attorney, Agent, or Firm* — Muir Patent Law, PLLC (57) ABSTRACT

An imaging apparatus includes an illumination light source to output an illumination light, an illumination optical system to transmit the illumination light toward a sample, an imaging optical system to transmit light reflected from the sample, a stage to move the sample in a predetermined transfer direction, and a photographing unit to receive the reflected light. The imaging apparatus may include one or more diffraction grids located at conjugate focal planes of the sample. The operation of the photographing unit may be synchronized with a movement of the sample by the stage to obtain an image in accordance with a time delay integration method.

8 Claims, 9 Drawing Sheets

(56) References Cited

U.S. PATENT DOCUMENTS

2011/0075151 A1\* 3/2011 Jeong ................... G01N 21/956
 356/453
2011/0242312 A1 10/2011 Seki et al.
2014/0152797 A1 6/2014 Mitsuhiro et al.

\* cited by examiner

IMAGING APPARATUS AND IMAGING METHOD

PRIORITY STATEMENT

This application claims priority under 35 U.S.C. § 119 to Japanese Patent Application No. 2017-138724, filed on Jul. 18, 2017 in the Japanese Intellectual Property Office and to Korean Patent Application No. 10-2017-0135454, filed on Oct. 18, 2017 in the Korean Intellectual Property Office (KIPO), the contents of both of these applications being incorporated by reference in their entirety.

BACKGROUND

1. Field

Example embodiments relate to an imaging apparatus and an imaging method.

2. Description of the Related Art

As semiconductor devices become smaller, a defect size to be inspected by an optical semiconductor inspection apparatus may become smaller. As the defect size becomes smaller, inspecting the defect becomes more difficult. In the optical semiconductor inspection apparatus, improving optical resolution may be effective.

In general, the optical resolution may be improved by decreasing a wavelength of a light to be used and increasing NA (Numerical Aperture) of an objective lens. With respect to the decrease in wavelength, a convention optical semiconductor inspection apparatus may use a light in the deep UV range of about 260 nm. In some cases, a wide wavelength band covering a UV range of about 400 nm may be used.

With respect to an optical system, it may be difficult to secure a sufficient transmission coefficient in a wide wavelength band. With respect to a light source, it may be difficult to secure a light source having a wide wavelength band at deep UV with a sufficient brightness. With respect to NA, an objective lens of high NA, an aperture of nearly 0.9 may be used. In order to maintain high resolution, it may be required to suppress aberration to the extreme, but it may be very difficult to suppress aberration over the wide wavelength range. For the above reasons, using light with short wavelengths with an objective lens of high NA reach their limits and it is hard to expect drastic improvement in resolution.

As a method for high resolution, there is a structure illumination microscope (SIM) (for example, Japanese Patent Publication No. 2006-268004). In this method, a Moire interference effect occurring when a light with periodic stripes is illuminated on a sample may be used. A high frequency component of the sample pattern may be shifted to a low frequency side of the illumination pattern by the Moire interference effect. In this technique, a frequency range over cut-off frequency, which is not resolved in the optical system, is shifted to be under the cut-off frequency, thereby enabling the frequency range to be resolved. From a plurality of photographed images by the illumination of the stripe shape with different phases, Moire interference component is separated and rearranged in a frequency space to regenerate an image. Similar to the strip shape of different directions, resolution in a plurality of directions is improved. Japanese Patent Publication No. 2006-268004 is herein incorporated by reference in its entirety.

For example, a conventional method may include the following operations. (1) A diffraction grid is positioned at a conjugate focal plane of a sample of an illumination optical system and an illumination light with a periodic strip shape is irradiated on a sample. (2) Images by the illumination of different directions and different phases are obtained. (3) An image is obtained by image processing. (4) The images of different directions/phases are synthesized by the image processing.

In the method, the images are obtained in different conditions from the same object, and image regeneration/synthesis is performed by the image processing, and accordingly, an image regeneration time takes longer. Thus, when the method is used in the semiconductor inspection apparatus, inspection time increases.

SUMMARY

Example embodiments provide an imaging apparatus and an imaging method capable of reducing an imaging time and improving optical resolution.

According to example embodiments, an imaging apparatus includes an illumination light source to output illumination light, a first diffraction grid positioned at a conjugate focal plane of a sample of an illumination optical system and transmitting the illumination light toward a sample, a second diffraction grid positioned at a conjugate focal plane of the sample of an imaging optical system and transmitting a light reflected from the sample on which the illumination light is incident, a stage to move the sample in a predetermined transfer direction, and a photographing unit to receive the reflected light from the sample through the second diffraction grid and synchronized with a movement of the sample according to the stage to photograph in time delay integration method.

In example embodiments, the first diffraction grid and the second diffraction grid may be optically identical to each other.

In example embodiments, the first diffraction grid and the second diffraction grid may include different types of grid patterns arranged in the transfer direction.

In example embodiments, the first diffraction grid and the second diffraction grid may include a grid pattern which is inclined with respect to the transfer direction.

In example embodiments, the first diffraction grid and the second diffraction grid may include a grid pattern having a period corresponding to a resolution limit which is determined by numerical aperture of the illumination optical system and the imaging optical system and a wavelength of the illumination light.

In example embodiments, the second diffraction grid and the photographing unit may be installed adjacent to each other.

According to example embodiments, an imaging apparatus includes an illumination light source to output an illumination light, a diffraction grid positioned at a conjugate focal plane of a sample of an imaging optical system and transmitting the illumination light toward a sample and a light reflected from the sample on which the illumination light is incident, a stage to move the sample in a predetermined transfer direction, and a photographing unit to receive the reflected light from the sample through the diffraction grid and synchronized with a movement of the sample according to the stage to photograph in time delay integration method.

According to example embodiments, in an imaging method, an illumination light source to output an illumination light, a first diffraction grid positioned at a conjugate focal plane of a sample of an illumination optical system and transmitting the illumination light toward a sample, a second diffraction grid positioned at a conjugate focal plane of the sample of an imaging optical system and transmitting a light reflected from the sample on which the illumination light is incident, and a stage to move the sample in a predetermined transfer direction are used. The reflected light from the sample is received through the second diffraction grid and is photographed in time delay integration method in synchronization with a movement of the sample according to the stage, by a photographing unit.

According to example embodiments, in an imaging method, an illumination light source to output an illumination light, a diffraction grid positioned at a conjugate focal plane of a sample of an imaging optical system and transmitting the illumination light toward a sample and a light reflected from the sample on which the illumination light is incident, and a stage to move the sample in a predetermined transfer direction are used. The reflected light from the sample is received through the diffraction grid and is photographed in time delay integration method in synchronization with a movement of the sample according to the stage, by a photographing unit.

According to example embodiments, an imaging time may be reduced and an optical resolution may be improved.

BRIEF DESCRIPTION OF THE DRAWINGS

Example embodiments will be more clearly understood from the following detailed description taken in conjunction with the accompanying drawings. FIGS. 1 to 10 represent non-limiting, example embodiments as described herein.

DETAILED DESCRIPTION OF EXAMPLE EMBODIMENTS

Hereinafter, example embodiments will be explained in detail with reference to the accompanying drawings.

First Example Embodiment

Figure 1:
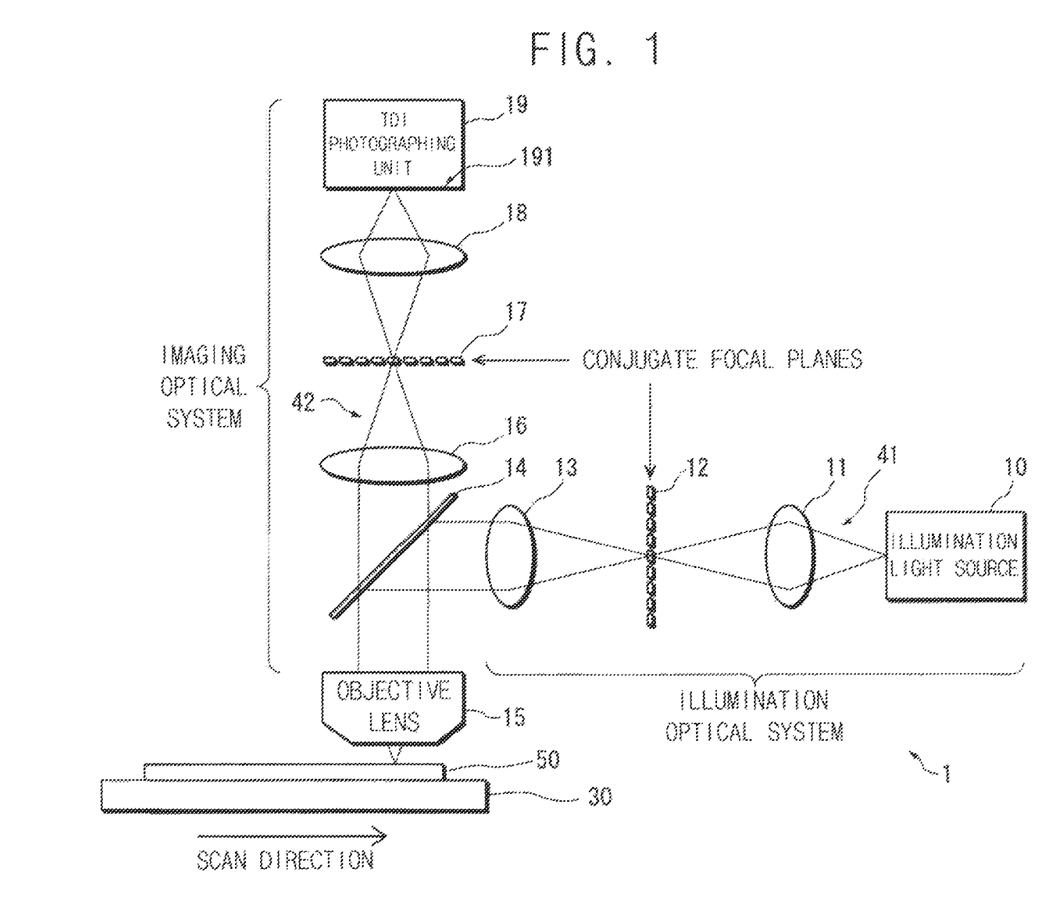
FIG. 1 is a schematic diagram illustrating an imaging device in accordance with a first example embodiment.

FIG. 1 is a schematic diagram illustrating an imaging device 1 in accordance with a first example embodiment, when viewed from the side. The imaging device 1 illustrated in FIG. 1 may be used to capture an image of a sample 50, such as a wafer. The imaging device 1, for example, may form an optical semiconductor inspection apparatus.

The imaging device 1 illustrated in FIG. 1 may include an illumination light source 10, a relay lens 11, a diffraction grid 12, a relay lens 13, a beam splitter 14, an objective lens 15, a relay lens 16, a diffraction grid 17, a relay lens 18, a TDI (Time Delay Integration) photographing unit 19 such as a TDI camera, and a stage 30. In the imaging device 1 illustrated in FIG. 1, the illumination light source 10, the relay lens 11, the diffraction grid 12 and the relay lens 13 may constitute an illumination optical system. The illumination optical system may irradiate an illumination light 41 output from the illumination light source 10 onto the sample 50 through the beam splitter 14 and the objective lens 15. The beam splitter 14, the relay lens 16, the diffraction grid 17, the relay lens 18 and the TDI photographing unit 19 may constitute an imaging optical system. The imaging optical system may transmit and focus light 42 reflected from the sample 50 and condensed by the objective lens 15 to a photographing surface 191 of the TDI photographing unit 19. The diffraction grid 12 may be positioned at a conjugate focal plane of sample 50 in the illumination optical system. The diffraction grid 17 may be positioned at another conjugate focal plane of the sample 50 in the imaging optical system. The conjugate focal planes may be image-forming conjugate focal planes that are part of an image-forming conjugate set of focal planes, including the conjugate focal planes where diffraction grids 12 and 17 are positioned, the object plane where the sample 50 is located and the camera image plane (also referred to as camera focal plane) of the TDI photographing unit 19 (e.g., the photographing surface 191 which may correspond to the surface of the image sensor of the photographing unit 19). Each of the diffraction grids 12 and 17 may be positioned to be coplanar with the respective conjugate focal plane at where it is positioned. During photographing, the stage 30 may have the sample 50 mounted on its upper surface and may move at a predetermined speed in a scan direction. The diffraction grid 12 and the diffraction grid 17 may be a transmission type diffraction grid (the grid forming openings allowing light to transmit through the grid), and may be structurally identical or at least optically identical. For example, the diffraction grid 12 and the diffraction grid 17 may be formed of grids of the same or geometrically similar patterns. For example, corresponding light blocking elements of the diffraction grid 12 and the diffraction grid 17 may have the same geometric shape, the same alignment, the same widths and spaced apart at the same pitch. When different grid patterns are implemented in the diffraction grids 12 and 17 (e.g., such as grid patterns 12-1~12-n as discussed herein with respect to FIG. 4), the grid type and orientation of the light blocking elements of each grid pattern in diffraction grid 12 may correspond to that of diffraction grid 17. For example, corresponding grid patterns (having the same or optically equivalent grid pattern—e.g., same or optically equivalent light blocking element width, spacing, orientation, etc.) of diffraction grids 12 and 17 are located at conjugate points of the conjugate focal planes where the diffraction girds 12 and 17 are located. The illumination light source 10, the stage 30 and the TDI photographing unit 19 may be controlled by a controller, such as by a computer (not illustrated). The computer may be a general purpose computer or may be dedicated hardware or firmware (e.g., an electronic or optical circuit, such as application-specific hardware, such as, for example, a digital signal processor (DSP) or a field-programmable gate array (FPGA)). The photographing unit 19 may comprise an image sensor, such as a charge coupled device CCD image sensor or a CMOS image sensor. The image sensor may provide pixel image data (e.g., as described herein with respect to pixels 190) to the computer (e.g., in the form of digital image data) and the computer may perform the integration of the time delay integration and form an integrated image as described herein (e.g., may obtain the image information from the image sensor column by column and integrate the image information to obtain image 74). Alternatively, the TDI photographing unit 19 may comprise a camera that includes hardware (e.g., controller) to perform the integration of the time delay integration as described herein.

In the imaging device illustrated in FIG. 1, the illumination light 41 emitted from the illumination light source 10 may pass through the relay lens 11 to be directed to the diffraction grid 12 installed at a sample conjugate surface in an illumination side (e.g., in the illumination optical system). The illumination light 41 may penetrate the diffraction grid 12 and the relay lens 13 and may be reflected by the beam splitter 14, and then may be irradiated onto the sample 50 through the objective lens 15. The illumination light 41 irradiated onto the sample 50 may have an intensity distribution corresponding to a grid pattern of the diffraction grid 12. The light 42 reflected from the sample 50 may pass through the objective lens 15, the beam splitter 14 and the relay lens 16 to be directed to the diffraction grid 17 installed at a sample conjugate surface in an imaging side (e.g., in the imaging optical system). The reflected light 42 may penetrate the diffraction grid 17 and the relay lens 18 and may be incident onto the photographing surface 191 of the TDI photographing unit 19. The light incident onto the photographing surface 191 may have an intensity distribution corresponding to the patterns of the diffraction grid 12 and 17, as well as the features of the sample 50. An image of the sample 50 may be photographed by the TDI photographing unit 19.

Figure 2:
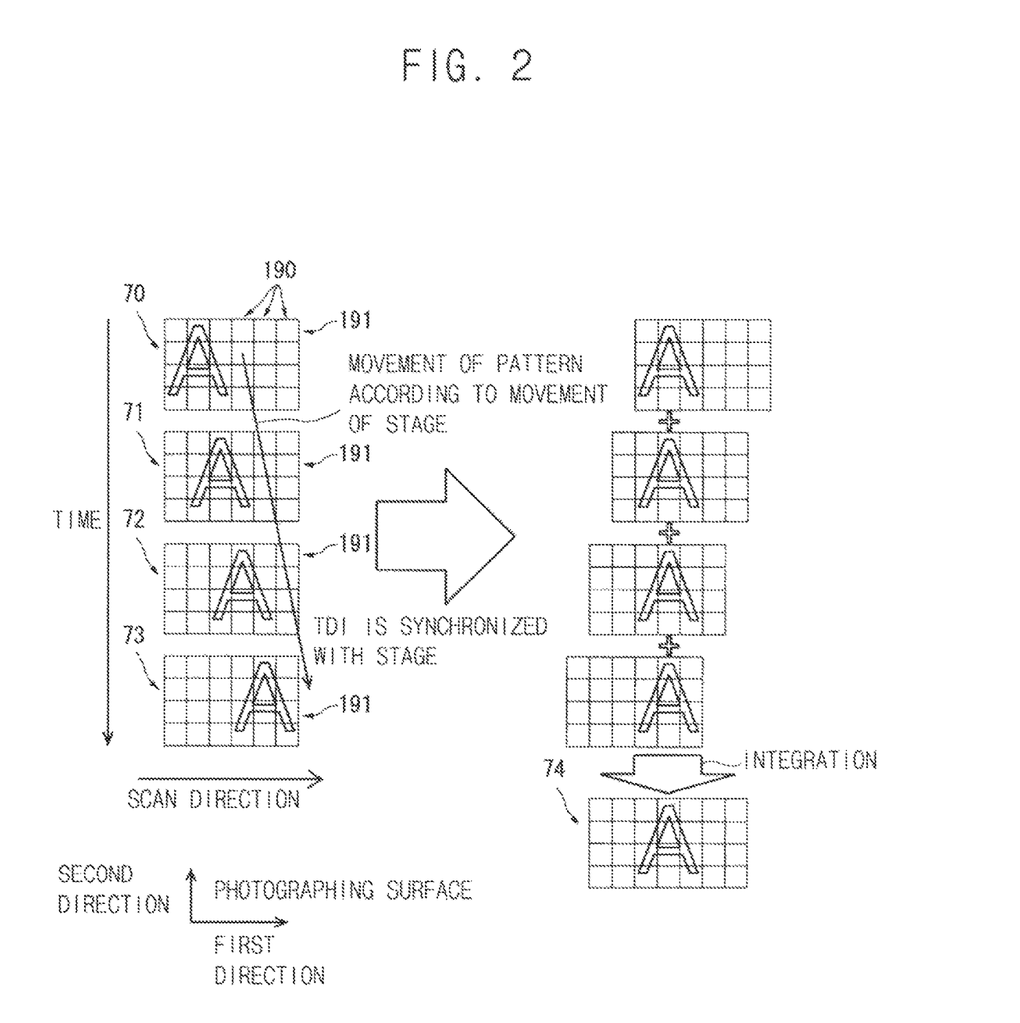
FIG. 2 is a view illustrating an example of an operation of the imaging device 1 of FIG. 1.

Hereinafter, a configuration and operation of the TDI (Time Delay Integration) photographing unit 19 will be explained with reference to FIG. 2. To assist in explaining the operation of the TDI photographing unit 19, the example images illustrated in FIG. 2 show an image of the letter "A"—it may be appreciated that different resulting images may result when using the imaging device 1 illustrated in FIG. 1 including the diffraction grid 12 and the diffraction grid 17. The TDI photographing unit 19 may include an image sensor, such as a CCD (Charge-Coupled Device) image sensor or a CMOS image sensor. The image sensor may include a plurality of pixels 190 arranged in a two dimensional matrix of rows and columns. FIG. 2 illustrates a photographing surface 191 (which may correspond to a surface of the image sensor) on which an image is focused by the image optical system to be captured by the image sensor. The photographing surface 191 may correspond to the image focal plane of a camera of the photographing unit 19 and be a surface of the image sensor forming pixels 190. The pixels 190 of the image sensor may be arranged as a plurality of columns of pixels (referenced by a TDI step number) and arranged as a plurality of rows of pixels. In the example of FIG. 2, each rows of pixels extends in the first direction (left to right in FIG. 2) and each column of pixels 190 extends in a second direction (here, perpendicular to the first direction—bottom to top in FIG. 2). It should be appreciated that a column of pixels in FIG. 2 may correspond to what may be typically referred to as a row of pixels in an image sensor.

For every cycle of obtaining image information from pixels 190 of the image sensor, each pixel 190 may accumulate electric charge over a predetermined exposure time period. The exposure period may start and stop at the same time for all of the pixels 190 or the exposure time periods may be staggered. For example, each column of pixels in FIG. 2 may be exposed to an image (provided by the imaging optical system) over an exposure period having concurrent start and end times, while the exposure periods of the different columns of pixel 190 may be staggered so that exposure period start times (and exposure period end times) are regularly spaced apart in a cycle of exposing and obtaining corresponding image data from the pixels 191 of entire pixel array. The TDI photographing unit 19 may sequentially transmit the electric charges accumulated in each pixel 190 in units of a line, (e.g., charges of a column of pixels may be sensed and output at the same time, followed by sensing and output charges of the next column, etc., so that column by column, the electric charges accumulated by the pixels 190 in an exposure period are sensed and output by the image sensor). The amount of accumulated charge of a pixel may correspond to an intensity of light received by the pixel over the previous exposure period. Thus, each column of pixels provide image information corresponding to the portion of the image provided by imaging optical system during the previous exposure period.

This column by column charge transmission direction (left to right direction in FIG. 2) may be matched with the scan direction (movement direction) of the stage 30 and a transmission timing of the image information of a column (e.g., electric charge) may be synchronized with the movement of the stage 30. Thus, the reflected light 42 from the same portion of the sample 50 may impinge on and be sensed from different columns of pixels 190 of the image sensor. It should be appreciated that the "scan direction" shown in FIG. 2 in connection with photographing surface 191 refers to the optical equivalent of the transfer direction (or scan direction) of the stage 30 (e.g., movement of sample 50 by stage 30 in a transfer direction of stage 30 causes an equivalent movement in a scan direction of an image at the conjugate focal plane at which photographing surface 191 (e.g., image sensor) is positioned). In FIG. 2, the number of rows of pixels of the photographing surface 191 is four (4) and the number of columns of pixels is six (6) for simplicity of explanation, however, the number of rows of pixels and the number of columns of pixels may be, for example, in the hundreds the thousands or more.

As illustrated in FIG. 2, when the image projected on the photographing surface 191 moves (represented as images 70, 71, 72 and 73 in FIG. 2) according to the movement of the stage 30, the following photograph result may be obtained from the TDI photographing unit 19. Operation of the TDI photographing unit 19 may be synchronized with the movement of the stage 30, such as synchronizing exposure periods of columns of the pixels 190 and/or synchronizing transmission of image information of pixels 190 (e.g., column by column transmission of electric charges accumulated in the pixels 190). For example, assuming n columns of pixels are to have their electric charges accumulated and transmitted from pixels 190, if each column of pixels 190 has equal width and has accumulated charges output at equally spaced time intervals over a cycle of reading the full array of pixels 190, the time period t for transmitting the image information of the full array of pixels 190 column by column may substantially be the same as the time period for the image projected onto the photographing surface 191 to move the width of one column of pixels 190. For example, the time between successive exposure cycles (e.g., between start times of successive exposure cycles) of each column of pixels 190 may be equal to the time period for the image projected onto the photographing surface 191 to move the width of one column of pixels 190, or equal to n×[the time period for the image projected onto the photographing surface 191 to move the width of one column of pixels 190] where n is an integer equal to one or more.

Thus, the portion of the sample 50 imaged, projected onto and sensed by a first column of pixels 190 may be the same as the portion of the sample 50 imaged, projected and sensed by a second column of pixels 190 (the first and second columns may be immediately adjacent columns or spaced apart by n−1 columns, where n is the integer equal to one or more). For example, the first column of pixels 190 (e.g., left most) may be exposed to the reflected light 42 from the same portion of the sample 50 with respect to image 70 as is the second column of pixels 190 with respect to image 71. As such, as the transmission of electric charge is repeatedly performed for the same imaged portions of sample 50, the corresponding image information obtained from different columns of pixels 190 over different exposure cycles of the pixel array may be integrated (e.g., combined or averaged) to obtain the image 74. Such integration may be referred to as a time delay integration method. Although the example of FIG. 2 illustrates every column of pixels of the array of pixels 191 receiving the same imaged portion of sample 50 and integrating image information from all columns of pixels 190, other implementations may integrate image information obtained from only a subset of the columns of the pixels 191.

Figure 3:
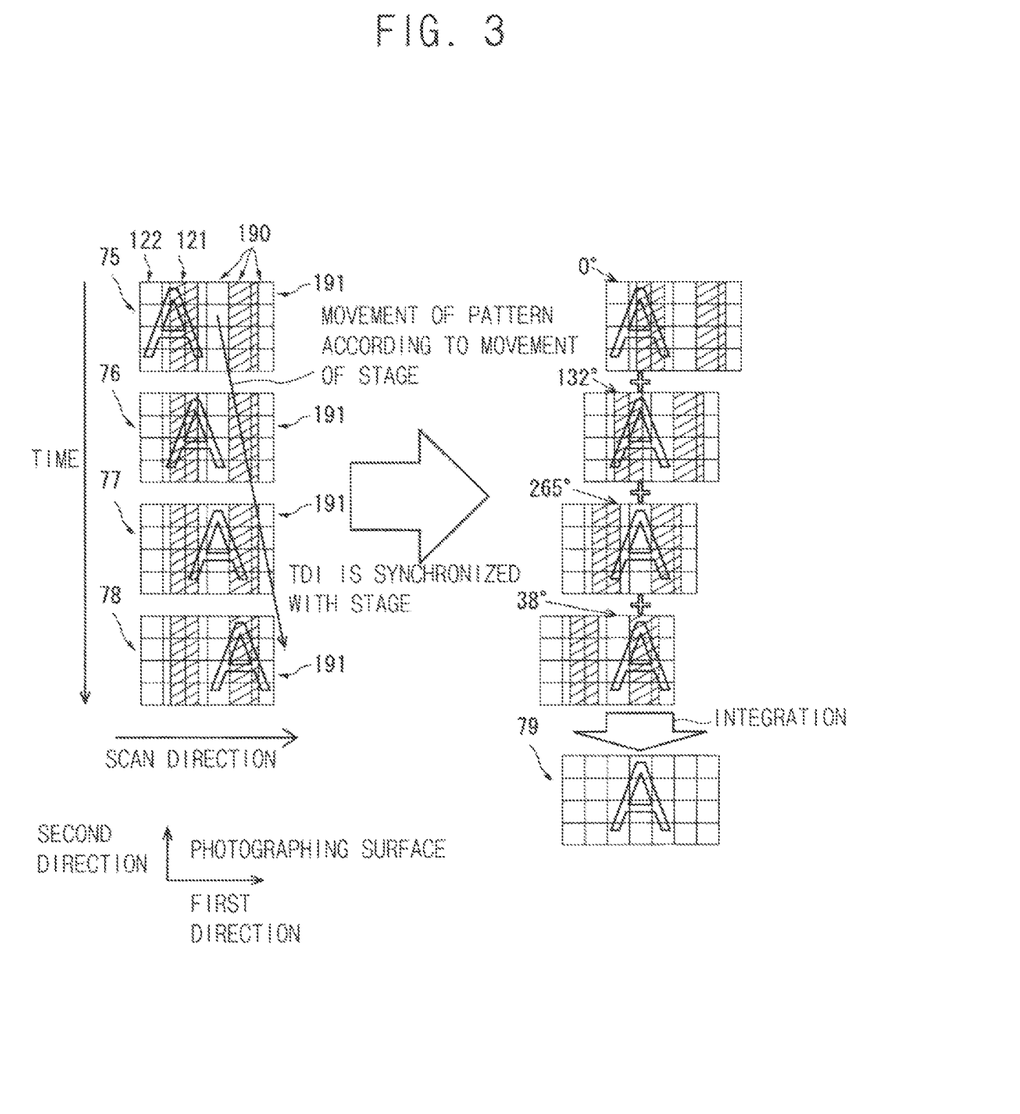
FIG. 3 is a view illustrating an example of an operation of the imaging device 1 of FIG. 1.

Then, an example of an operation in case that the imaging device 1 illustrated in FIG. 1 includes the diffraction grid 12 and the diffraction grid 17 will be explained with reference to FIG. 3. In this case, for example, repetitive diffraction grid stripes may generate a dark portion 121 (hashed portion in FIG. 3) interposed between bright portions 122 of the image projected onto the photographing surface 191. Because the diffraction grid 12 and/or 17 is/are installed fixedly in the conjugate focal plane of the sample 50, as the stage 30 moves, the image projected on the photographing surface 191 is changed (here, sequentially between images 75, 76, 77 and 78), but the repetitive dark portions 121 and the bright portions 122 resulting from the diffraction grid stripes may not move. For example, if the diffraction grid 12 is installed in the conjugate focal plane of the sample 50 (e.g., corresponding to the upper illuminated surface of the sample 50) to provide an illumination of the diffraction grid pattern, because the diffraction grid 12 is fixed, the TDI photographing unit 19 may obtain image 79 which integrates the images phase shifted by 0°, 132°, 265° and 38° respectively.

Figure 4:
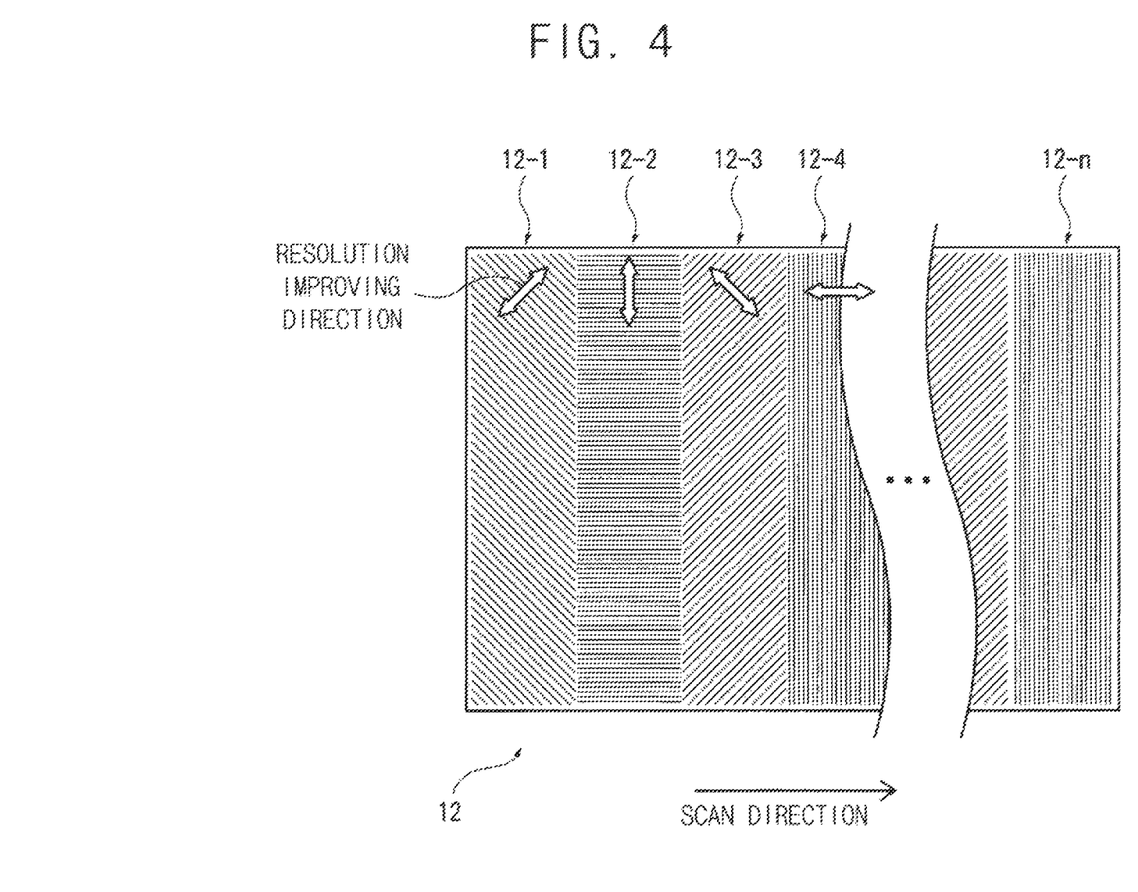
FIG. 4 is a view illustrating an example of a configuration of a diffraction grid 12 of FIG. 1.

As illustrated in FIG. 4, the diffraction grid 12 may include different types of grid patterns 12-1~12-n having different directions of grid lines. Each of the grid patterns may be elongated in a direction perpendicular with respect to the scan direction and the grid patterns may be arranged side by side with respect to the scan direction. "Scan direction" in connection with diffraction grids positioned at a conjugate focal plane refers to the optical equivalent of the transfer direction (or scan direction) of the stage 30 at the conjugate focal planes (e.g., movement of sample 50 by stage 30 in a transfer direction of stage 30 causes an equivalent movement in a scan direction of an image at the conjugate focal plane at which grid 17 is positioned). The grid patterns 12-1~12-n may be formed integrally in one base or each may be formed in a different respective base. Each of the grid patterns 12-1~12-n may include a repetitive pattern, such as grid lines that are inclined at a corresponding angle (with respect to the scan direction) different from other grid line inclination angles of the grid patterns 12-1~12-n. The grid pattern 12-1~12-n may have a pattern period corresponding to a resolution limit (referred to as diffraction limit or resolution) which is determined by NA (numerical aperture) of lens arranged in the illumination optical system and the imaging optical system and a wavelength of the illumination light 41. The resolution may be improved in a direction as denoted with a white arrow corresponding to the inclined angle of each grid pattern 12-1~12-n. When the diffraction grid 12 includes the different types of the grid patterns 12-1~12-n arranged in the scan direction, the TDI photographing unit 19 may integrate the grid patterns of the different grid directions and the images of the sample 50 together. The TDI photographing unit 19 may output one image where columns of the one image integrates corresponding columns of images (such as 75, 76, 77 and 78) including dark portions 121 resulting from all direction/phase grid patterns on the diffraction grid 12. Thus, the TDI photographing unit 19 may automatically obtain the image of the sample 50 using a plurality of different grid patterns in a single scan. By using the TDI photographing unit 19, the image of the sample 50 may be obtained from superimposition as described herein and may avoid the need to preform image processing of an image.

As illustrated in FIG. 1, in this embodiment, the diffraction grid 17 having a structurally identical structure (or optically identical structure) with the diffraction grid 12 may be positioned at the conjugate focal plane of the sample of the imaging optical system (e.g., coplanar with a conjugate focal plane of the sample in the imaging side). Accordingly, as a grid pattern of the diffraction grid 17 may be adjusted to be identical to the grid pattern of the diffraction grid 12 in the illumination side, in a photographed image of the TDI photographing unit 19, image regeneration may be automatically and optically performed. The image regeneration may comprise the diffraction grid 17 arranged to have the same frequency/phase with the illumination side diffraction pattern of diffraction grid 12 to cause Moire interference. Thus, a frequency component as a super-resolution (described above) which penetrates the objective lens by the Moire interference returns to the original frequency component. Additionally, a Moire interference component remaining by only the illumination grid may be removed (See Non-patent literature [W. Lukosz, M. Marchand, "Optische Abbildung unter Uberschreitung der beugungsbedingten Auflosungsgrenze", J. Mod. Opt. 10 (1963) 241-255]). Accordingly, in the image photographed by the TDI photographing unit 19, the image regeneration may be possible without performing image processing.

As mentioned above, the imaging device 1 in accordance with this embodiment may include the illumination light source 10 outputting the illumination light, the diffraction grid 12 (first diffraction grid) installed in the conjugate focal plane of the sample of the illumination optical system and transmitting the illumination light 41 to the sample, the diffraction grid 17 (second diffraction grid) installed in the conjugate focal plane of the sample of the imaging optical system and transmitting the reflected light 42 from the sample, the stage 30 moving the sample in the scan direction (transfer direction), and the TDI photographing unit 19 (photographing unit) synchronized with the movement of the sample 50 and photographing in the TDI method (time delay integration method). According to the imaging device 1 in accordance with this embodiment, an imaging time may be reduced and an optical resolution may be improved.

Further, in the imaging device 1 in accordance with this embodiment, the diffraction grid 12 and the diffraction grid 17 may include a grid pattern having a period corresponding to a resolution limit. Such resolution limit may be determined by NA (numerical aperture) of the illumination optical system and the imaging optical system. The diffraction grid 12 and the diffraction grid 17 may be optically identical to each other. The diffraction grid 12 and the diffraction grid 17 may include different types of grid patterns arranged in the scan direction. The diffraction grid 12 and the diffraction grid 17 may include a grid pattern which is inclined at a different angle with respect to the scan direction.

The imaging device 1 in accordance with this embodiment may use the TDI photographing unit 19 and include the diffraction grid 12 and the diffraction grid 17 installed respectively in the conjugate focal plane of the samples of the illumination optical system and the imaging optical system, to thereby provide a structured illumination. That is, the imaging device 1 in accordance with this embodiment may include diffraction grids of predetermined pattern and pitch installed in respective conjugate focal planes of the sample (sample conjugate surfaces) of the illumination optical system/imaging optical system and may integrate/image the light passing through two diffraction grids (12 and 17). The diffraction grid (12 and 17) may include a pattern having a period corresponding to a resolution limit which is determined by wavelength/NA of the optical system. Different grid patterns (or diffraction grids) may be arranged in the scan direction within the field of vision, and the TDI photographing unit 19 may integrate the images of the diffraction grid pattern of different directions in a single scan to output one image. The relay lens of the imaging optical system may have NA greater than NA right before the sample conjugate surface of the imaging optical system determined as a middle magnifying factor between NA of the objection lens and the conjugate focal plane of the sample of the imaging optical system.

According to the imaging device 1 in accordance with this embodiment, when the pitch of the diffraction grid is the resolution limit pitch of the objective lens, resolution may be improved as compared to a conventional optical system, such as at least twice the resolution limit of a conventional optical system as determined by the NA of such a conventional optical system. When compared with a conventional structured illumination, images of different directions/phases may be obtained in a single scan, and the image regeneration/synthesis may be automatically and optically performed without image processing. Therefore, the imaging speed or inspection speed may not be decreased.

Figure 5:
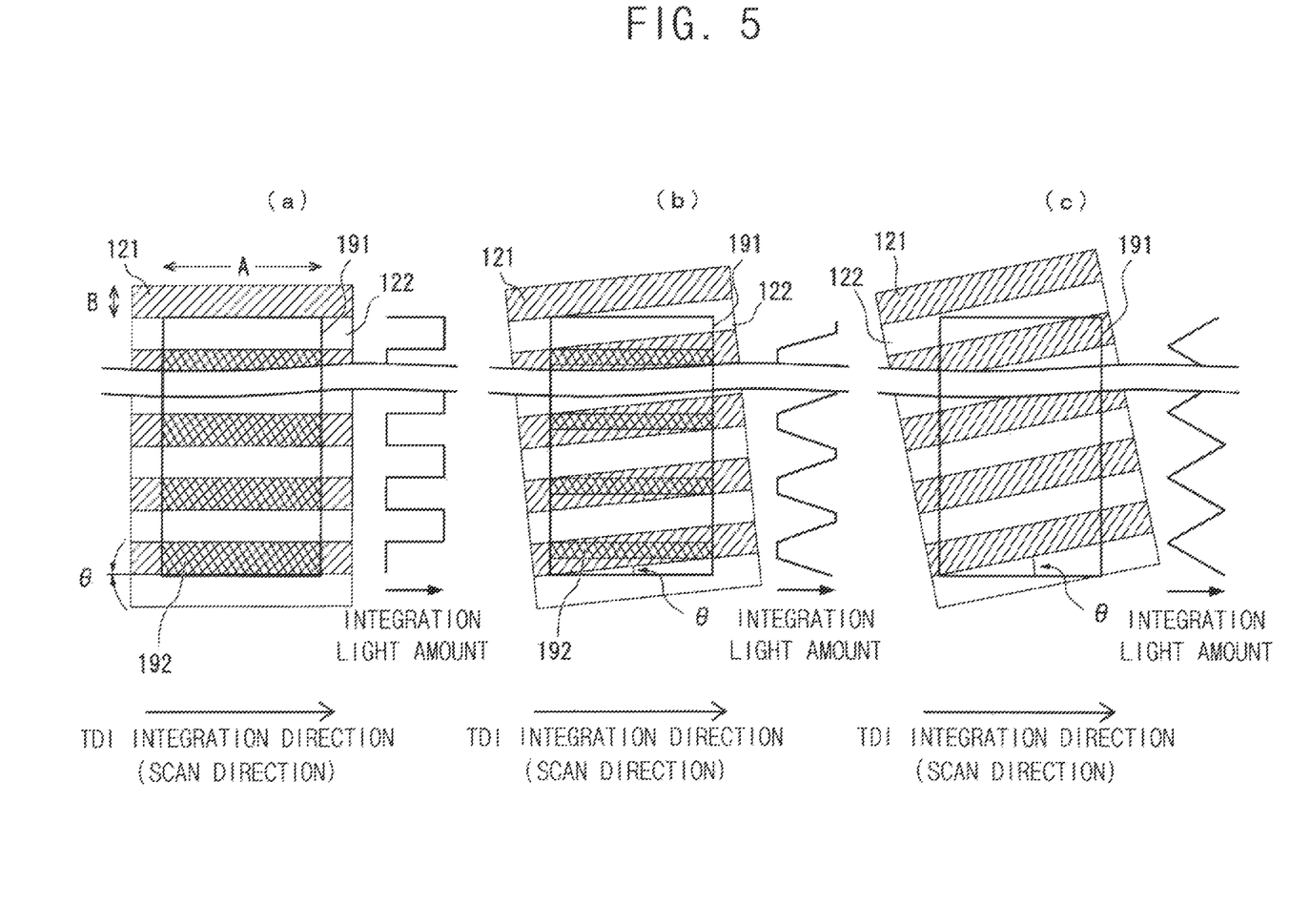
FIG. 5 is a view illustrating an example of an operation of the imaging device 1 of FIG. 1.

Then, an inclination angle of the grid pattern of the diffraction grid 12 will be explained with reference to FIG. 5. FIG. 5 is a view illustrating a relation between an integration light amount of the TDI imaging unit 19 and the inclination angle of the diffraction grid 12. FIG. 5(*a*) represents a case that an angle θ between the TDI integration direction and the direction of the dark portion 121 and the bright portion 121 of the diffraction grid stripes (hereinafter, referred to as diffraction grid stripe direction) is 0°. FIG. 5(*b*) represents a case that the angle θ between the TDI integration direction and the diffraction grid stripe direction satisfies (A·tan θ<B). Here, A is a width of the photographing surface 191 in the TDI integration direction, and B is a width of the dark portion 121 of the diffraction grid stripe. FIG. 5(*c*) represents a case that an angle θ between the TDI integration direction and the diffraction grid stripe direction satisfies (A·tan θ>B).

As illustrated in FIG. 5, a size of an insensible region 192 (region overlapped always with the dark portion 121, during photograph) formed in the photographing surface 191 may be changed by the angle θ between the TDI integration direction and the diffraction grid stripe direction. In the case that θ=0° in FIG. 5(*a*), the insensible region 192 may be the maximum, and an integration light amount may be changed in a square wave shape. In the case that A·tan θ<B in FIG. 5(*b*), there is the insensible region 192, and the integration light amount may be changed in a trapezoidal wave shape. In the case that A·tan θ>B in FIG. 5(*c*), there is not the insensible region 192, and the integration light amount may be changed in a sawtooth wave shape.

As illustrated in FIG. 5, in the case that A·tan θ<B, an insensible region may be formed while integration. Therefore, the inclined angle θ of the diffraction grid stripe direction may be determined as a value satisfy A·tan θ>B.

Figure 6:
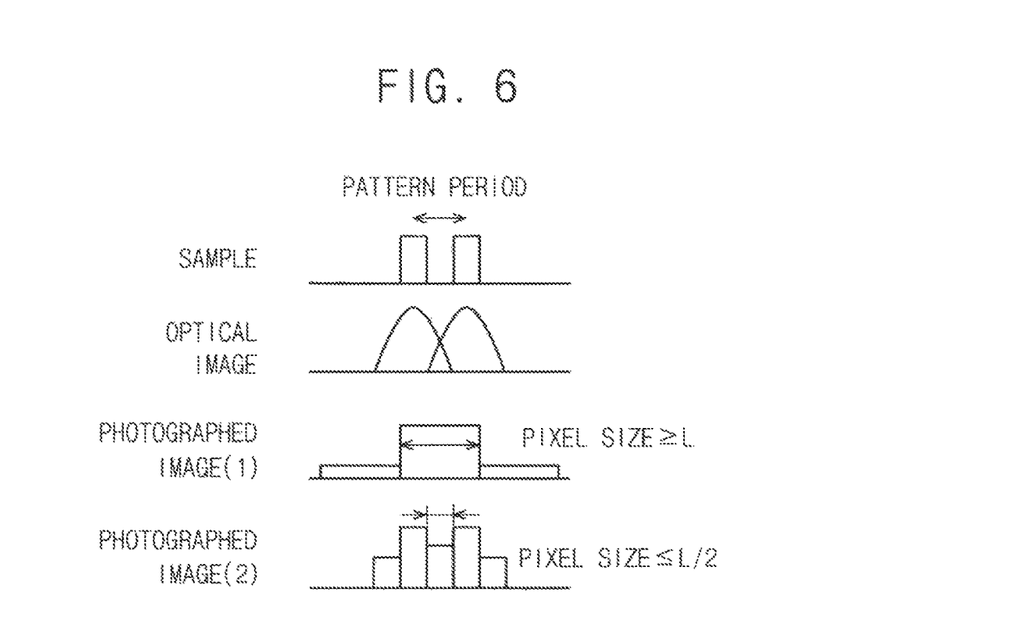
FIG. 6 is a view illustrating an example of an operation of the imaging device 1 of FIG. 1.

Then, a size of the pixel 190 of the TDI photographing unit 19 will be explained with reference to FIG. 6. FIG. 6 illustrates a change of a shape of the sample 50, an optical image projected onto the photographing surface 191 of an image sensor, and a pixel value of each pixels of photographed images 1 and 2 obtained from the TDI photographing unit 19 in the order from top to bottom, with a transverse axis being the first direction or the second direction. As illustrated in FIG. 6, in case that the shape of the sample 50 to be photographed is a rectangular parallelepiped shape of a pattern period L, and the period L is greater than the resolution limit of the imaging optical system, the resulting optical image may be, for example, a shape of two mountains. In this case, when the pixel size L, the pixel size is greater than a distance of the period L of the sample pattern, the photographed image 1 may not be resolved (photographed image (1) illustrating the output of three adjacent pixels receiving the optical image obtained from the sample). On the other hand, when the pixel size ≤L/2, the pixel size is less than the pattern period of the sample, the photographed image 2 may be resolved (photographed image (2) illustrating the output of five adjacent pixels receiving the optical image obtained from the sample). That is, the pixel size is preferably less than ½ of the resolution limit of the optical system.

Figure 7:
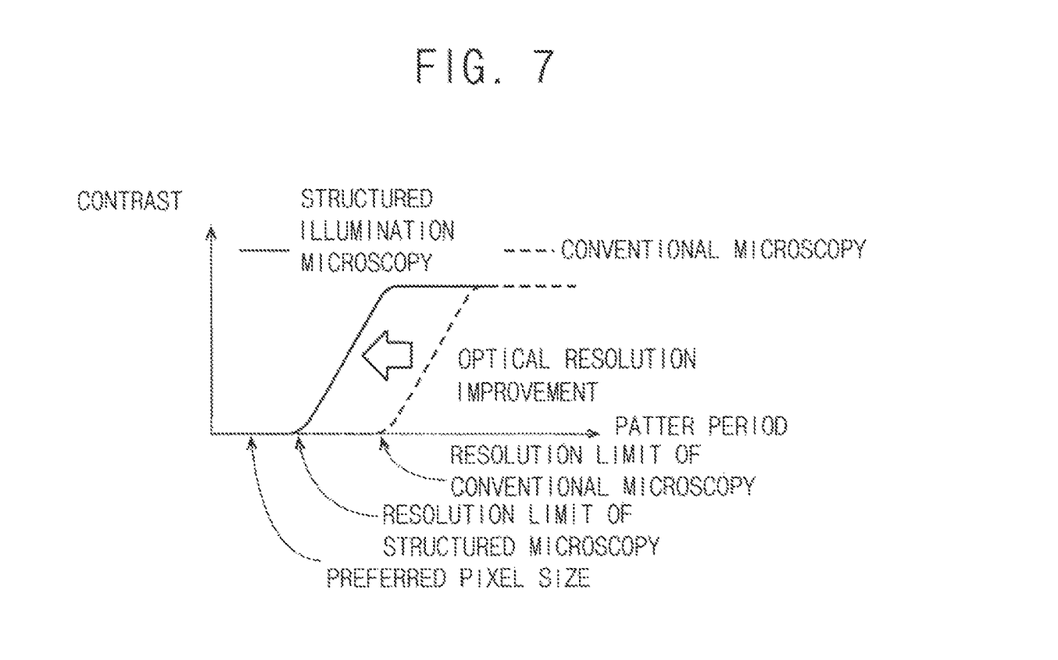
FIG. 7 is a view illustrating an example of an operation of the imaging device 1 of FIG. 1.

FIG. 7 is a view illustrating a relation between contrast of the optical image in the photographing surface of a microscope and the pattern period L in FIG. 6. In a structured illumination microscope, the resolution limit may be about ½ of the pattern period, when compared with a conventional microscope. Accordingly, the pixel size of the structured illumination microscope is preferably less than ½ of a pattern size of an improved resolution limit.

Additionally, the configuration of this embodiment may not be limited thereto. For example, in the imaging device 1, the number of the relay lenses may be increased, a display device or a memory device, or an image processing device recognizing a defective pattern on the sample 50 may be installed.

Second Example Embodiment

Figure 8:
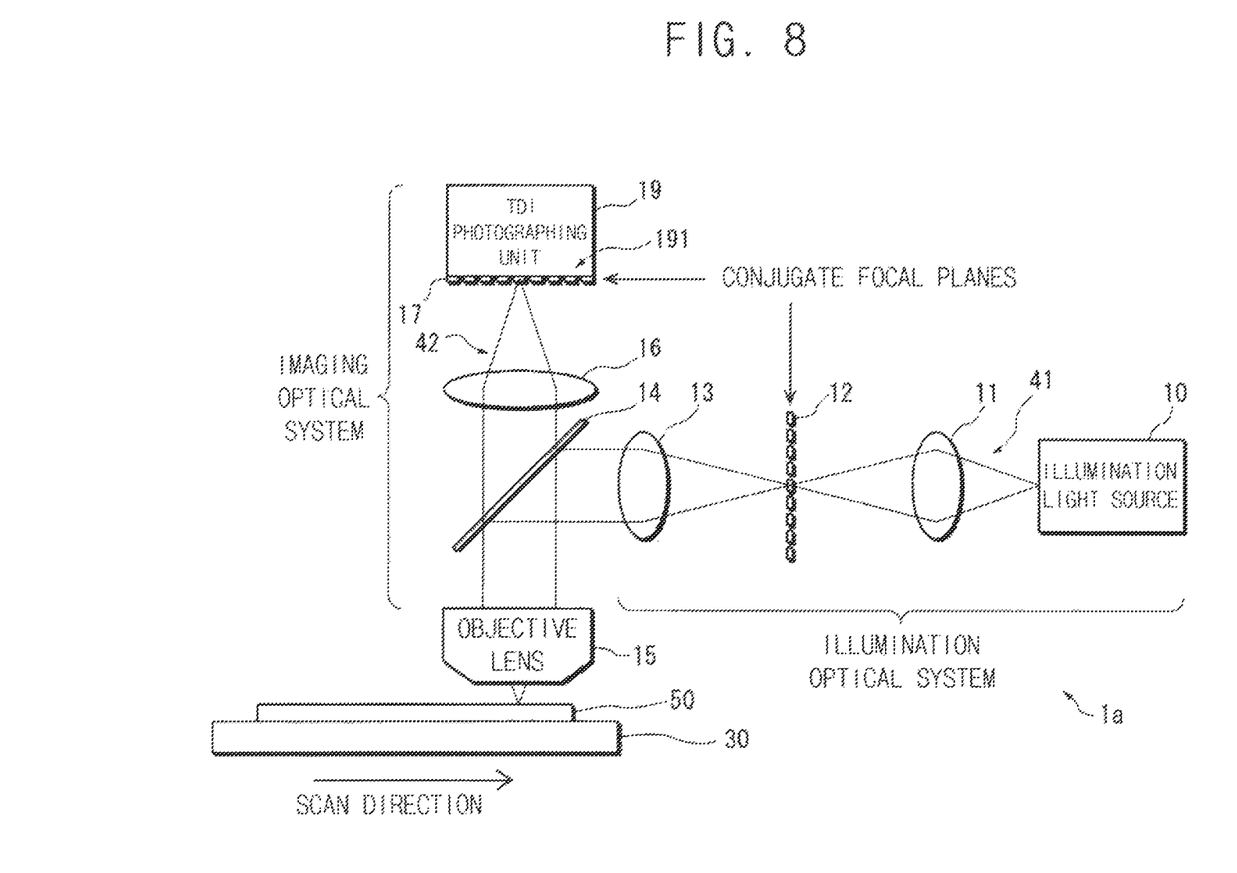
FIG. 8 is a schematic diagram illustrating an imaging device in accordance with a second example embodiment.

FIG. 8 is a schematic diagram illustrating an imaging device 1*a* in accordance with a second example embodiment, when viewed from the side. In FIG. 8, same reference numerals will be referred to the same elements as the first example embodiment illustrated in FIG. 1 and any further explanation concerning the above elements will be omitted. The imaging device 1*a* illustrated in FIG. 8 is different from the imaging device 1 illustrated in FIG. 1 as follows. In the imaging device 1a illustrated in FIG. 8, both the diffraction grid 17 (second diffraction grid) and the TDI photographing unit 19 are installed at a conjugate focal plane of the sample. Further, in the imaging device 1a illustrated in FIG. 8, the relay lens 18 illustrated in FIG. 1 is omitted. In the imaging device 1a illustrated in FIG. 8, the TDI photographing unit 19 photographs the sample 50 at the conjugate focal plane of the sample. Other configurations and operations may be substantially the same as or similar to the imaging device 1 of the first example embodiment.

According to the imaging device 1a in accordance with this embodiment, similar to the imaging device 1 of the first example embodiment, resolution may be improved to twice that of a conventional optical system as limited by the NA of the conventional optical system. When compared with a conventional structured illumination, images of different directions/phases may be obtained in a single scan, and image regeneration/synthesis may be automatically and optically performed without requiring image processing of an entire image. Therefore, an imaging speed or inspection speed may not be decreased.

Third Example Embodiment

Figure 9:
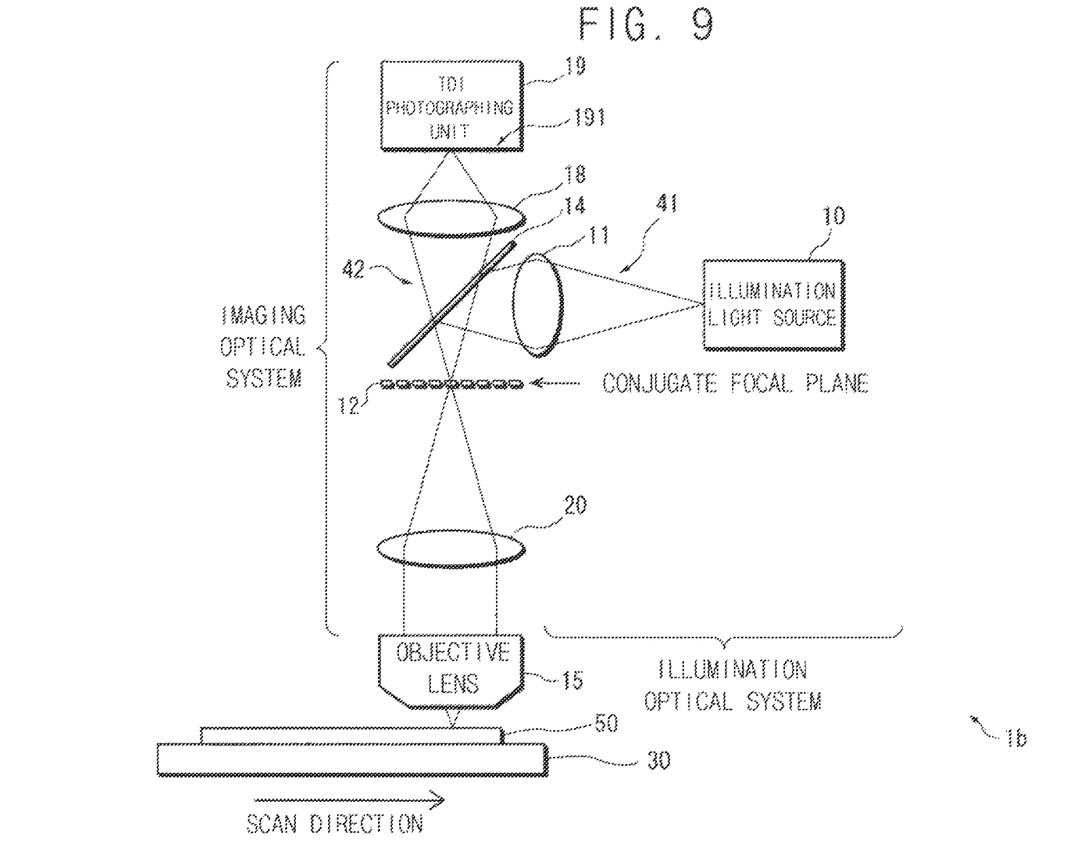
FIG. 9 is a schematic diagram illustrating an imaging device in accordance with a third example embodiment.

FIG. 9 is a schematic diagram illustrating an imaging device 1b in accordance with a third example embodiment, when viewed from the side. In FIG. 9, same reference numerals will be referred to the same elements as the first example embodiment illustrated in FIG. 1 and any further explanation concerning the above elements will be omitted. The imaging device 1b illustrated in FIG. 9 is different from the imaging device 1 illustrated in FIG. 1 as follows. In the imaging device 1b illustrated in FIG. 9, a diffraction grid 17 (second diffraction grid), a relay lens 13 and a relay lens 16 are omitted, and a new relay lens 20 is installed. Further, in the imaging device 1b illustrated in FIG. 9, a diffraction grid 12 is positioned at a conjugate focal plane of the sample between a beam splitter 14 and the relay lens 20. The relay lens 20 may transmit a reflected light 42 to form an image at the conjugate focal plane of the sample. In third example embodiment, an optical system where the illumination optical system/imaging optical system share a common conjugate focal plane of the sample is provided; one diffraction grid 12 may be used for the illumination optical system and the imaging optical system. A position alignment of the diffraction grids of the illumination optical system/imaging optical system may be avoided.

According to the imaging device 1b in accordance with this embodiment, similar to the imaging device 1 of the first example embodiment, resolution may be improved to twice that of a conventional optical system as limited by the NA of the conventional optical system. When compared with a conventional structured illumination, images of different directions/phases may be obtained in a single scan, and image regeneration/synthesis may be automatically and optically performed without image processing. Therefore, an imaging speed or inspection speed may not be decreased.

Modified Example

Figure 10:
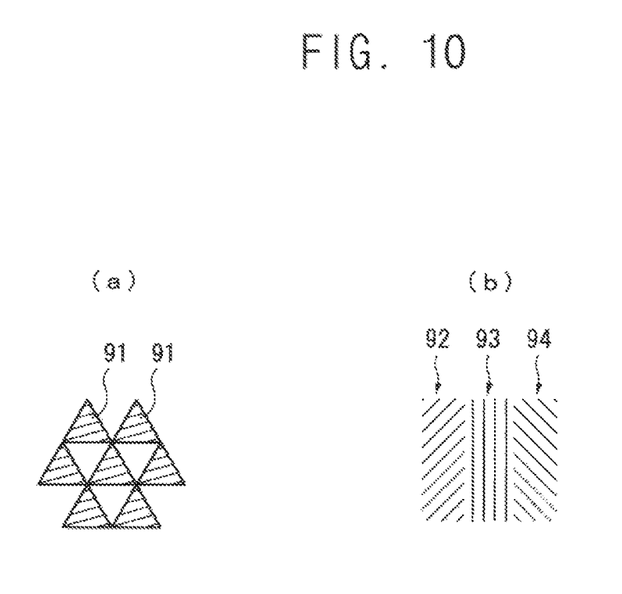
FIG. 10 is a view illustrating a modified example of an example embodiment.

Then, a modified embodiment of a grid pattern of the above-mentioned diffraction grid 12 and diffraction grid 17 will be explained with reference to FIG. 10. In the above-mentioned explanation, it was described that the grid pattern of the diffraction grid 12 has a periodic structure of line and space, for example, as illustrated in FIG. 4. However, the grid pattern of the diffraction grid 12 and the diffraction grid 17 may take different forms. The grid pattern of the diffraction grid 12 and the diffraction grid 17 may be a grid pattern which includes, for example, a plurality of triangular shaped grids 91 as illustrated in FIG. 10(a). Although linear elements of the grid are shown to be formed in the same direction within the triangle shaped grids 91, these linear elements may be arranged in different directions as described with respect to FIG. 4. In this case, resolution may be improved in a direction perpendicular to each side of the triangle grid 91. That is, the same resolution improvement effect as grid patterns 92, 93 and 94 having three different periodic structures of line and space as illustrated in FIG. 10(b) may be obtained. On the other hand, the grid pattern may not be limited to the triangular grid, for example, the grid pattern may be a grid pattern which includes, for example, a plurality of oval grids.

The foregoing is illustrative of example embodiments and is not to be construed as limiting thereof. Although a few example embodiments have been described, those skilled in the art will readily appreciate that many modifications are possible in example embodiments without materially departing from the novel teachings and advantages of the present invention. Accordingly, all such modifications are intended to be included within the scope of example embodiments as defined in the claims.

What is claimed is:

1. An imaging apparatus, comprising:
   a stage to position a sample in an object plane and to move the sample in a predetermined transfer direction;
   an illumination light source to output an illumination light;
   a first diffraction grid positioned at a first conjugate focal plane that is within an illumination optical system, the first diffraction grid configured to transmit the illumination light received from the illumination light source toward a sample on the stage;
   a second diffraction grid positioned at a second conjugate focal plane that is within an imaging optical system, the second diffraction grid configured to transmit light reflected from the sample; and
   an image sensor to receive the light reflected from the sample transmitted by the second diffraction grid,
   wherein the first conjugate focal plane, the second conjugate focal plane and the object plane are elements of the same conjugate set of focal planes of the imaging apparatus, and
   wherein the image sensor is configured to operate repetitively at a timing in synchronization with a movement of the stage to obtain a time delay integration image.

2. The imaging apparatus of claim 1, wherein the first diffraction grid and the second diffraction grid are optically identical to each other.

3. The imaging apparatus of claim 1, wherein the first diffraction grid and the second diffraction grid each comprise different types of grid patterns arranged in a first direction optically corresponding to the transfer direction.

4. The imaging apparatus of claim 1, wherein the first diffraction grid and the second diffraction grid each comprise a grid pattern having linear grid elements obliquely inclined with respect to a first direction optically corresponding to the transfer direction.

5. The imaging apparatus of claim 1, wherein the first diffraction grid and the second diffraction grid each comprise a grid pattern having a period corresponding to a resolution limit which is determined by a numerical aperture of the illumination optical system and the imaging optical system and a wavelength of the illumination light.

6. The imaging apparatus of claim 1, wherein the second diffraction grid and image sensor are positioned adjacent to each other.

7. An imaging apparatus, comprising:
- a stage to move position a sample in an object plane and move the sample in a predetermined transfer direction;
- an illumination light source to output an illumination light;
- a diffraction grid positioned at a conjugate focal plane within an imaging optical system, the diffraction grid positioned to transmit the illumination light output by the illumination light source toward the sample and to transmit light reflected from the sample; and
- an image sensor positioned to receive the reflected light from the sample transmitted by the diffraction grid,
- wherein the conjugate focal plane and the object plane are elements of the same conjugate set of focal planes of the imaging apparatus, and
- wherein the image sensor is configured to operate repetitively at a timing in synchronization with a movement of the stage to obtain a time delay integration image.

8. An imaging method, comprising:
- providing a sample on a stage at an object plane and moving the stage in a predetermined transfer direction;
- outputting illumination light from an illumination light source;
- using a first diffraction grid positioned at a first conjugate focal plane that is within an illumination optical system, transmitting the illumination light toward a sample;
- using a second diffraction grid positioned at a second conjugate focal plane that is within an imaging optical system, transmitting light reflected from the sample on which the illumination light is incident; and
- exposing an image sensor with light reflected from the sample and transmitted by the second diffraction grid,
- wherein the first conjugate focal plane, the second conjugate focal plane and the object plane are elements of the same conjugate set of focal planes, and
- wherein operation of the image sensor is synchronized with a movement of the sample to form an image according to a time delay integration method.

* * * * *